(12) United States Patent
Bradford

(10) Patent No.: US 8,778,947 B2
(45) Date of Patent: Jul. 15, 2014

(54) METHODS OF ADMINISTERING PIRFENIDONE THERAPY

(71) Applicant: Intermune, Inc., Brisbane, CA (US)

(72) Inventor: Williamson Z. Bradford, Wilson, WY (US)

(73) Assignee: Intermune, Inc., Brisbane, CA (US)

(*) Notice: Subject to any disclaimer, the term of this patent is extended or adjusted under 35 U.S.C. 154(b) by 0 days.

(21) Appl. No.: 14/015,857

(22) Filed: Aug. 30, 2013

(65) Prior Publication Data
US 2014/0066484 A1    Mar. 6, 2014

Related U.S. Application Data

(60) Provisional application No. 61/696,044, filed on Aug. 31, 2012, provisional application No. 61/709,125, filed on Oct. 2, 2012, provisional application No. 61/749,026, filed on Jan. 4, 2013, provisional application No. 61/775,240, filed on Mar. 8, 2013, provisional application No. 61/842,706, filed on Jul. 3, 2013.

(51) Int. Cl.
*A61K 31/497*     (2006.01)
*A61K 31/435*     (2006.01)

(52) U.S. Cl.
USPC ............................... 514/253.07; 514/277

(58) Field of Classification Search
USPC .................................. 514/253.07, 277
See application file for complete search history.

(56) References Cited

U.S. PATENT DOCUMENTS

| | | |
|---|---|---|
| 5,310,562 A | 5/1994 | Margolin |
| 5,518,729 A | 5/1996 | Margolin |
| 5,716,632 A | 2/1998 | Margolin |
| 7,407,973 B2 | 8/2008 | Ozes et al. |
| 7,566,729 B1 | 7/2009 | Bradford et al. |
| 7,605,173 B2 | 10/2009 | Seth |
| 7,635,707 B1 | 12/2009 | Bradford et al. |
| 7,696,236 B2 | 4/2010 | Bradford |
| 7,728,013 B2 | 6/2010 | Blatt et al. |
| 7,767,700 B2 | 8/2010 | Bradford |
| 7,816,383 B1 | 10/2010 | Bradford et al. |
| 7,910,610 B1 | 3/2011 | Bradford et al. |
| 8,013,002 B2 | 9/2011 | Bradford et al. |
| 8,318,780 B2 | 11/2012 | Bradford et al. |
| 2006/0110358 A1 | 5/2006 | Hsu |
| 2007/0053877 A1 | 3/2007 | Crager et al. |
| 2007/0054842 A1 | 3/2007 | Blatt et al. |
| 2007/0072181 A1 | 3/2007 | Blatt |
| 2007/0092488 A1 | 4/2007 | Strieter et al. |
| 2007/0117841 A1 | 5/2007 | Ozes et al. |
| 2007/0172446 A1 | 7/2007 | Blatt |
| 2007/0203202 A1 | 8/2007 | Robinson et al. |
| 2007/0203203 A1 | 8/2007 | Tao et al. |
| 2008/0003635 A1 | 1/2008 | Ozes et al. |
| 2008/0019942 A1 | 1/2008 | Seiwert et al. |
| 2008/0194644 A1 | 8/2008 | Bradford |
| 2008/0206329 A1 | 8/2008 | Verma et al. |
| 2008/0287508 A1 | 11/2008 | Robinson et al. |
| 2008/0319026 A1 | 12/2008 | Gant et al. |
| 2009/0170804 A1 | 7/2009 | Phillips et al. |
| 2009/0191265 A1 | 7/2009 | Radhakrishnan et al. |
| 2009/0197923 A1 | 8/2009 | Bradford |
| 2009/0318455 A1 | 12/2009 | Kossen et al. |
| 2010/0152250 A1 | 6/2010 | Radhakrishnan et al. |
| 2010/0324097 A1 | 12/2010 | Bradford |
| 2011/0136876 A1 | 6/2011 | Robinson et al. |
| 2011/0166186 A1 | 7/2011 | Bradford et al. |
| 2011/0172277 A1 | 7/2011 | Bradford et al. |
| 2011/0263656 A1 | 10/2011 | Bradford et al. |
| 2011/0319453 A1 | 12/2011 | Bradford et al. |
| 2012/0015985 A1 | 1/2012 | Bradford et al. |
| 2012/0088801 A1 | 4/2012 | Bradford et al. |
| 2012/0192861 A1 | 8/2012 | Surber |
| 2013/0030024 A1 | 1/2013 | Bradford et al. |
| 2013/0045997 A1 | 2/2013 | Bradford et al. |

FOREIGN PATENT DOCUMENTS

| | | |
|---|---|---|
| EP | 1138329 A2 | 10/2001 |
| EP | 1880722 A1 | 1/2008 |
| EP | 2324831 B1 | 5/2011 |
| WO | WO-2009/035598 A1 | 3/2009 |

OTHER PUBLICATIONS

Aloxi® (palonosetron) package insert, Rev. Feb. 2008 ("Palonosetron package insert").
Antoniu, Pirfenidone for the treatment of idiopathic pulmonary fibrosis. *Exp. Opin. Invest. Drugs*, 15: 823-8 (2006).
Azuma et al., Double-blind, placebo-controlled trial of pirfenidone in patients with idiopathic pulmonary fibrosis. *Am. J. Respir. Crit. Care Med.* 171: 1040-7 (2005).
Babovic-Vuksanovic et al., Phase I of pirfenidone in children with neurofibromatosis 1 and plexiform neurofibromas. *Pediatric Neurol.*, 365: 293-300 (2007).
Bauer et al., A survey of population analysis methods and software for complex pharmacokinetic and pharmacodynamic models with examples, *AAPS J.*, 9(1):E60-83 (2007).
Brosen et al., Fluvoxamine is a potent inhibitor of cytochrome P4501A2, *Biochem. Pharmacol.*, 45(6):1211-4 (1993).
Brosen, The pharmacogenetics of the selective serotonin reuptake inhibitors, *Clin. Investig.*, 71(12):1002-9 (1993).
BuSpar® (buspirone HCl, USP) package insert.
Castro et al., Biomarkers in systemic sclerosis. *Biomark Med.* 4: 133-47 (2010).
Cho et al., Pirfenidone slows renal function decline in patients with focal segmental glomerulosclerosis. *Clin. J. Am. Soc. Nephrol.*, 2(5): 906-13 (2007).
Clozaril® (clozapine) package insert.
Collard et al., Plasma biomarker profiles in acute exacerbation of idiopathic pulmonary fibrosis. *Am. J. Physiol. Lung Cell Mol. Physiol.* 299: L3-7 (2010).

(Continued)

*Primary Examiner* — Raymond Henley, III
(74) *Attorney, Agent, or Firm* — Carolyn Tang; John Bendrick; Marshall, Gerstein & Borun LLP

(57) ABSTRACT

The disclosure relates to improved methods of administering pirfenidone therapy when ciprofloxacin is administered concomitantly.

18 Claims, 1 Drawing Sheet

(56) References Cited

OTHER PUBLICATIONS

Correspondence received from FDA.
Dolophine Hydrochloride (methadone hydrochloride) package insert.
Ebadi, Desk Reference of Clinical Pharmacology, Chapter 5, Food-Drug Interactions, p. 31-36 (2008).
Esbriet, Annex I: Summary of Product Characteristics, European Label (Feb. 2012).
European search report from EP 10250379.4, dated May 17, 2010.
European search report from EP 11006411.0, dated Mar. 8, 2012.
FDA Briefing Information for the Mar. 9, 2010 Meeting of the Pulmonary-Allergy Drugs Advisory Committee (Contains the Clinical Briefing Document (Banu Karimi-Shah, M.D., Clinical Reviewer, Division of Pulmonary and Allergy Products, NDA 22-535) beginning on p. 21), published at <http://www.fda.gov/downloads/AdvisoryCommittees/Committees MeetingMaterials/Drugs/Pulmonary-AllergyDrugsAdvisoryCommittee/UCM203081.pdf>.
Figgitt et al., Fluvoxamine. An updated review of its use in the management of adults with anxiety disorders, *Drugs*, 60(4):925-54 (2000).
Food and Drug Administration Center for Drug Evaluation and Research, Pulmonary-Allergy Drugs Advisory Committee (PADAC) Meeting Transcript (Tuesday, Mar. 9, 2010), published at <http://www.fda.gov/downloads/AdvisoryCommittees/CommitteesMeetingMaterials/Drugs/ Pulmonary-AllergyDrugsAdvisoryCommittee/UCM208806.pdf>.
Food and Drug Administration, Guidance of Industry Draft, Drug Interation Studies—Study Design, Data Analysis, and Implications for Dosing and Labeling, dated Sep. 2006.
Food and Drug Adminstration Preliminary Concept Paper, Drug Interaction Studies—Study Design, Data Analysis, and Implications for Dosing and Labeling, dated Oct. 1, 2004.
Fuhr et al., Inhibitory effect of grapefruit juice and its bitter principal, naringenin, on CYP1A2 dependent metabolism of caffeine in man. *Br. J. Clin. Pharmac.*, 35:431-6 (1993).
Girennavar et al., Furocoumarins from grapefruit juice and their effect on human CYP 3A4 and CYP 1B1 isoenzymes. *Bioorg. Med. Chem.*, 14: 2606-12 (2006).
Girennavar et al., Potent inhibition of human cytochrome P450 3A4, 2D6, and 2C9 isoenzymes by grapefruit juice and its furocoumarins. *J. Food Sci.*, 72(8): C417-21 (2007).
Goosen et al., Bergamottin contribution to the grapefruit juice-felodipine interaction and disposition in humans. *Clin. Pharmacol. Therapeut.*, 76(6): 607-17 (2004).
Hanley et al., The effects of grapefruit juice on drug disposition. *Expert Opin. Drug. Metab. Toxicol.*, 7(3): 267-86 (2011).
He et al., Inactivation of cytochrome P45 3A4 by Bergamottin, a component of grapefruit juice. *Chem. Res. Toxicol.*, 11:252-9 (1998).
Hemeryck et al., Selective serotonin reuptake inhibitors and cytochrome P-450 mediated drug—drug interactions: An update, *Curr. Drug Metab.*, 3:13-37 (2002).
Horn et al. "Get to Know and Enzyme: CYP1A2," http://www.pharmacytimes.com/publications/issue/2007/2007-11/2007-11-8279, 3 pages. (2007).
Hummers, The current state of biomarkers in systemic sclerosis. *Curr. Rheumatol. Rep.* 12: 34-9 (2010).
Inderal® (propranolol hydrochloride, long-acting capsules) package insert.
Inderal® (propranolol hydrochloride capsule, extended release) package insert.
InterMune Briefing Information for the Mar. 9, 2010 Meeting of the Pulmonary-Allergy Drugs Advisory Committee, published at <http://www.fda.gov/downloads/AdvisoryCommittees/CommitteesMeetingMaterials/Drugs/Pulmonary-AllergyDrugsAdvisoryCommittee/UCM203083.pdf>.
InterMune Canada, Inc., PrEsbrietTM Pirfenidone Capsules 267 mg Product Monograph (Oct. 19, 2012).
International Search Report and Written Opinion of related case PCT/US10/058943, (2010).
Ito et al., Impact of parallel pathways of drug elimination and multiple cytochrome P450 involvement on drug-drug interactions: CYP2D6 paradigm. *Drug Metab. Dispos.* 33(6): 837-44 (2005).
Jeppesen et al., Dose-dependent inhibition of CYPIA2, CYP2C19 and CYP2D6 by citalopram, fluoxetine, fluovaxamine and paroxetine. *Eur. J. Clin. Pharmacol.*, 41(1):73-8 (1996).
Karjalainen et al., In vitro inhibition of CYP1A2 by model inhibitors, anti-inflammatory analgesics and female sex steroids: Predictability of in vivo interactions. *Basic Clin. Pharmacol. Toxicol.* 103(2): 157-65 (2008).
Kroon, Drug interactions with smoking. *Am. J. Health-System Pharm.*, 64(18): 1917-21 (2007).
Landi et al., Human cytochrome P4501A2. *IARC Scientific Publications*, 148:173-95 (1999).
Leape et al., Systems analysis of adverse drug events. ADE Prevention Study Group, JAMA, 274(1):35-43 (1995).
Lexotan (bromazepam) package insert.
Malarone® (atovaquone and proguanil hydrochloride) package insert.
McGinnity et al., Integrated in vitro analysis for the in vivo prediction of cytochrome P450-mediated drug—drug interactions. *Drug Metab. Dispos.* 36(6): 1126-34 (2008).
Mexitil® (mexiletine hydrochloride, USP) package insert.
Nakano, The promotion and inhibition of metabolism by co-administered drugs and countermeasures against them, *Igaku no Ayumi*, vol. 170:959-62 (2009).
Naropin® (ropivacaine hydrochloride monohydrate) package insert.
Odansetron product information from the UK Medicines and Healthcare Products Regulatory Agency ("Odansetron UK product information").
Olesen et al., Fluvoxamine-clozapine drug interaction: Inhibition in vitro of five cytochrome P450 isoforms involved in clozapine metabolism. *J. Clin. Psychopharmacol.*, 20(1): 35-42 (2000).
Opposition filed against European Patent 2 324 831 dated Jun. 28, 2012, filed by Herzog Fiesser & Partner on behalf of Sandoz AG.
Owen, Controlled-release fluvoxamine in obsessive-compulsive disorder and social phobia. *Drugs Today*, 44(12): 887-93 (2008).
Pirfenex Tablets 200 mg product label information (Mar. 2011).
Pirfenidone NDA 22-535 Pulmonary-Allergy Drugs Advisory Committee Mar. 9, 2010, slide deck (InterMune, Inc.), published at <http://www.fda.gov/downloads/AdvisoryCommittees/CommitteesMeetingMaterials/Drugs/Pulmonary-AllergyDrugsAdvisoryCommittee/UCM206399.pdf>.
Preskorn et al., Clinically relevant pharmacology of selective serotonin reuptake inhibitors. *Clin. Pharmacokin.*, 32(Suppl. 1): 1-21 (1997).
Pulmonary-Allergy Drugs Advisory Committee Meeting, Pirfenidone Capsules, NDA 22-535, S-000, Mar. 9, 2010, slide deck (U.S. Food and Drug Administration), published at <http://www.fda.gov/downloads/AdvisoryCommittees/CommitteesMeetingMaterials/Drugs/Pulmonary-AllergyDrugsAdvisoryCommittee/UCM206398.pdf>.
Quinidine Gluconate package insert.
Raghu et al., Treatment of idiopathic pulmonary fibrosis with a new antifibrotic agent, pirfenidone. *Am. J. Respir. Crit. Care Med.*, 159: 1061-9 (1999).
Raschetti et al., Suspected adverse drug events requiring emergency department visits or hospital admissions, *Eur. J. Clin. Pharmacol.*, 54(12):959-63 (1999).
Rasmussen et al., Selective serotonin reuptake inhibitors and theophylline metabolism in human liver microsomes: potent inhibition by fluvoxamine, *Br. J. Clin. Pharmacol.*, 39(2):151-9 (1995).
Remington's: the Science and Practice of Pharmacy, 17th Edition, vol. 1, p. 806 (1985).
Response to opposition filed in favor of European Patent 2 324 831 dated Feb. 8, 2013, filed by Potter Clarkson on behalf of Intermune Inc.
Richards et al., Peripheral blood proteins predict mortality in Idiopathic pulmonary fibrosis. *Am. J. Respir. Crit. Care Med.* 185: 67-76 (2012).
Sawada et al., Pharmacokinetics and interactions of antidepressants, *Nihon Rinsho*, vol. 59, issue 8 (Aug. 2009).

(56) References Cited

OTHER PUBLICATIONS

Scriabine et al., New developments in the therapy of pulmonary fibrosis. *Adv. Pharmacol.*, 57: 419-64 (2009).
Shigimura, On Pirfenidone Tablets, an Anti-Fibrosis Agent, Chiba Prefectural Pharmacists Association, (May 20, 2009).
Shionogi & Co. Ltd., Pirfenidone Glaspear tablet 200 mg Examination Report, Evaluation and Licensing Division, Pharmaceutical and Food Safety Bureau (Sep. 16, 2008).
Shionogi & Co., Ltd., Pirespa Tablet Packaging Label, Prepared Oct. 2008.
Shionogi & Co., Ltd., Pirespa Tablet Packaging Label, Revised Nov. 2011.
Shionogi & Co., Ltd., Pirespa Tablet Report on the Deliberation Results, Evaluation and Licensing Division, Pharmaceutical and Food Safety Bureau, Ministry of Health, Labour and Welfare (Sep. 16, 2008).
Stump et al., Management of grapefruit-drug interactions. *Am. Farm Physician*, 74(4): 605-8 (2006).
Taniguchi et al., Pirfenidone in idiopathic pulmonary fibrosis. *Eur. Respir. J.* and online supplement, 35:821-9 (2010).
Taniyama et al., The pharmacokinetics of the anti-fibrosis agent pifenidone when administered continuously to patients with pulmonary fibrosis and dialysis patients, *Rinshou Yakuri Jpn J Clin Pharmacol Ther.*, 31(2) (2000).
Tassaneeyakul et al., Inhibition selectivity of grapefruit juice components on human cytochrome P450. *Arch. Biochem. Biophys.*, 378(2): 356-63 (2000).
Thioridazine Hydrochloride package insert.
Tofranil (imipramine hydrochloride) package insert.
Tzouvelekis et al., Serum biomarkers in interstitial lung diseases. *Respir. Res.* 6: 78 (2005).
van den Blink et al., Serum biomarkers in idiopathic pulmonary fibrosis. *Pulm. Pharm. Ther.* 23: 515-20 (2010).
Vij et al., Peripheral blood biomarkers in idiopathic pulmonary fibrosis.*Transl. Res.* 159: 218-27 (2012).
Yoshimasu et al., Side Effects and Interactions of Antipsychotics (2003).
Zhang et al., Determination of the inhibitory potential of 6 fluoroquinolones on CYP1A2 and CYP2C9 in human liver microsomes. *Acta Pharmacol. Sin.* 29(12): 1507-14 (2008).
Zofran® (odansetron) package insert ("Odansetron package insert"), Apr. 2002.
Zyprexa® (olanzapine) package insert, Rev. Jan. 27, 2010 ("Olanzapine package insert").
International Search Report and Written Opinion of related case PCT/US13/57666 dated Jan. 16, 2014.
CIPRO® (ciprofloxacin hydrochloride) Tablets CIPRO (ciprofloxacin) Oral Suspension, 81532304, R.2; NDA 019537-020780 Cipro Tabs and Oral Susp FDA Approved, Feb. 25, 2011; accessed on Dec. 24, 2013: <http://www.pharma.bayer.com/html/pdf/Cipro_Tablets> and Oral Suspension PI.pdf; p. 2, Table—Adult Dosage Guidelines.

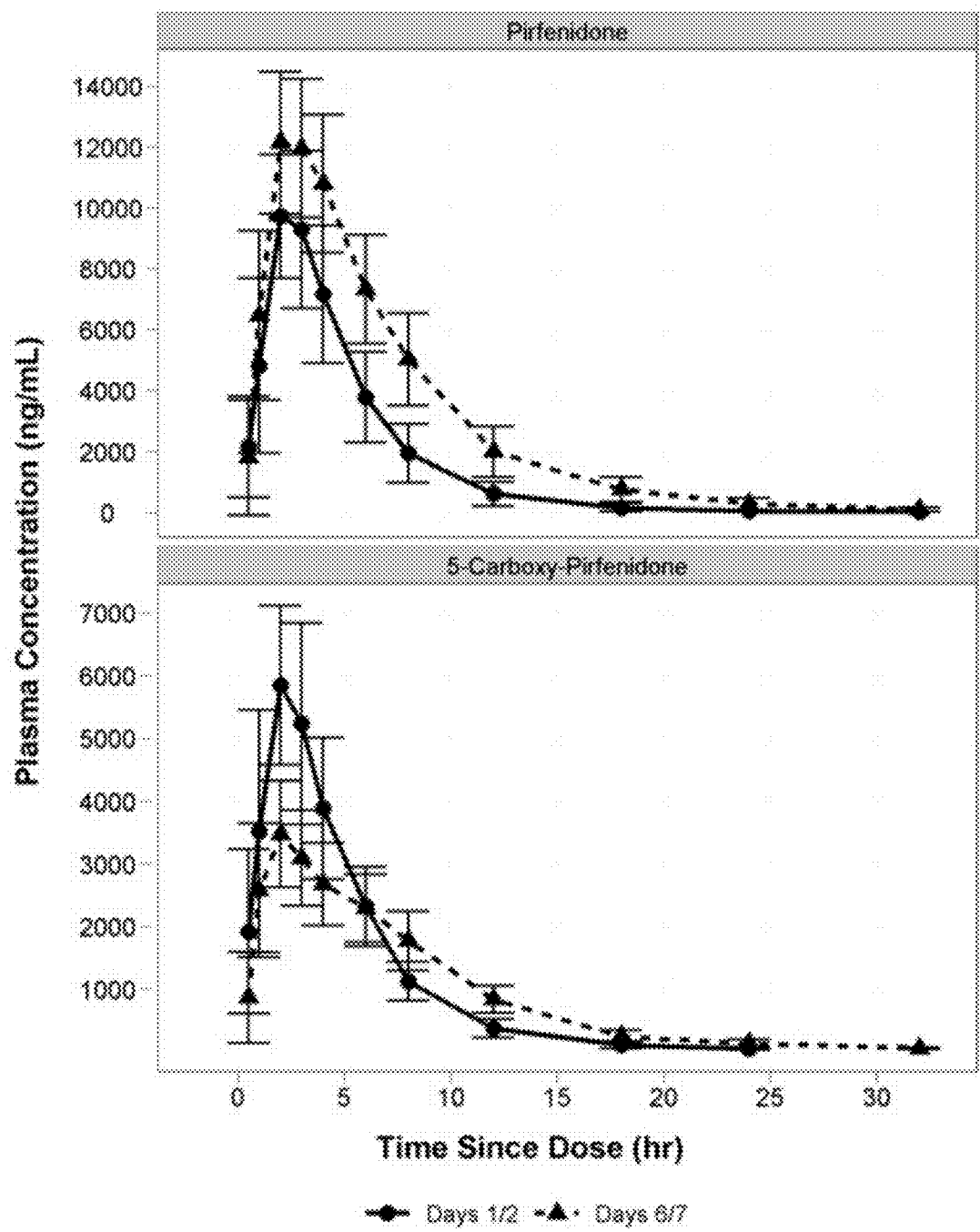

METHODS OF ADMINISTERING PIRFENIDONE THERAPY

CROSS-REFERENCE TO RELATED APPLICATIONS

This application claims the priority benefit under 35 U.S.C. §119(e) of Provisional U.S. Patent Application No. 61/696,044, filed Aug. 31, 2012; Provisional U.S. Patent Application No. 61/709,125, filed Oct. 2, 2012; Provisional U.S. Patent Application No. 61/749,026, filed Jan. 4, 2013; Provisional U.S. Patent Application No. 61/775,240, filed Mar. 8, 2013; and Provisional U.S. Patent Application No. 61/842,706, filed Jul. 3, 2013, each of which is incorporated herein by reference in their entirety.

FIELD OF THE INVENTION

The disclosure relates to improved methods of administering pirfenidone therapy when ciprofloxacin is administered concomitantly and to a novel therapeutic dose of pirfenidone.

BACKGROUND

Pirfenidone is a small molecule with a molecular weight of 185.23 daltons whose chemical name is 5-methyl-1-phenyl-2-(1H)-pyridone. Pirfenidone has anti-fibrotic properties and has been investigated for therapeutic benefits to patients suffering from various fibrotic conditions. It is approved in Japan for treatment of idiopathic pulmonary fibrosis (IPF) under the trade name Pirespa®, and in several European countries under the trade name Esbriet®.

Pirfenidone has been shown to be metabolized by various isoforms of the cytochrome P450 (CYP) protein [See the Report on the Deliberation Results, Evaluation and Licensing Division, Pharmaceutical and Food Safety Bureau, Ministry of Health Labour and Welfare, Sep. 16, 2008]. Specifically, several cytochrome P450 (CYP) isoforms (CYP1A2, 2C9, 2C19, 2D6 and 2E1) were reported to be involved in the earliest stages of oxidative metabolism of pirfenidone. More recently, it was reported that in vitro experiments showed that pirfenidone metabolism is predominantly carried out by CYP1A2 [U.S. Pat. No. 7,816,383, incorporated by reference herein in its entirety].

Ciprofloxacin is a broad spectrum antimicrobial agent. Ciprofloxacin hydrochloride, USP, a fluoroquinolone, is the monohydrochloride monohydrate salt of 1-cyclopropyl-6-fluoro-1,4-dihydro-4-oxo-7-(1-piperazinyl)-3-quinolinecarboxylic acid. It has a molecular weight of 385.8, its empirical formula is $C_{17}H_{18}FN_3O_3 \cdot HCl \cdot H_2O$ and its chemical structure is as follows:

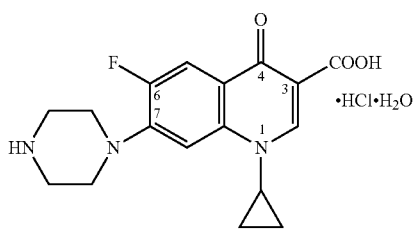 [SMILES: O=C(O)c1cn(C2CC2)c2cc(N3CCNCC3)c(F)cc2c1=O]

Ciprofloxacin was previously classified as a moderate inhibitor of CYP1A2 by the FDA [FDA Draft Guidance for Industry Drug Interaction Studies—Study Design, Data Analysis, and Implications for Dosing and Labeling, September 2006]; this description was recently revised in February 2012 [FDA Draft Guidance for Industry Drug Interaction Studies—Study Design, Data Analysis, Implications for Dosing, and Labeling Recommendations, February 2012].

SUMMARY OF THE INVENTION

The disclosure generally relates to improved use of pirfenidone and methods of administering pirfenidone to a patient in need of pirfenidone therapy, and to corresponding methods of preparing or packaging pirfenidone medicaments, containers, packages and kits. The disclosure also relates to pirfenidone for corresponding uses in treating a patient in need of pirfenidone therapy, including use of a novel therapeutic dose.

The present disclosure is based in part on the discovery that concomitant administration of pirfenidone at a dose of 801 mg (e.g., given three times per day for a total daily dose of 2403 mg/day) and ciprofloxacin at a dose of 750 mg (e.g., given twice daily for a total daily dose of 1500 mg/day), produces a modest but significant rise in pirfenidone exposure to about 1.8-fold, on average. Thus, for example, a patient receiving a daily dose of 2403 mg may be exposed to pirfenidone levels equivalent to a dose of about 4325 mg pirfenidone.

In one aspect, therefore, the disclosure relates to the discovery that ciprofloxacin should not be used (e.g., should be avoided) at a high dose of 750 mg or higher with pirfenidone, due to the potential for reduced clearance of pirfenidone and/or the potential for increased exposure to pirfenidone (about 1.8-fold the exposure as measured by area under the curve, AUC). Such improved uses and methods involve avoiding concomitant use of ciprofloxacin at a dose of 750 mg or higher, or 700 mg or higher, during pirfenidone administration (or avoiding concomitant use of pirfenidone during ciprofloxacin administration), as well as discontinuing pirfenidone during the time period of ciprofloxacin use.

In the first aspect, for example, the disclosure provides a method of administering pirfenidone therapy to a patient in need thereof, comprising administering to the patient a therapeutically effective amount of pirfenidone, and avoiding co-administration of ciprofloxacin at a dose of 750 mg or higher, e.g. 750 mg taken twice a day. In any of the aspects or embodiments of the disclosure, a method of administering pirfenidone therapy to a patient in need thereof is provided, comprising administering to the patient a therapeutically effective amount of pirfenidone, and avoiding co-administration of ciprofloxacin at a dose of between about 650 mg to about 850 mg, or between about 700 mg to about 800 mg, or higher. In some embodiments, the dose of ciprofloxacin is administered to the patient two times per day (i.e., BID), for a total daily dose of 1500 mg per day.

In embodiments of such methods, for example, pirfenidone at an oral dose of about 800 mg, or about 801 mg, is administered and concomitant dosing of ciprofloxacin at an oral dose of 750 mg or higher, or at a dose of between about 650 mg to about 850 mg, or between about 700 mg to about 800 mg, is avoided. In one embodiment, the disclosure provides a method wherein a dose of ciprofloxacin lower than 750 mg, or lower than 700 mg, or lower than 650 mg (for example, about 500 mg), is administered to the patient. In another embodiment, an alternative antibiotic therapy that is not ciprofloxacin is administered to the patient. Avoiding concomitant use of pirfenidone and ciprofloxacin at equivalent dosing by other routes is contemplated.

In the first aspect, the disclosure also provides methods of administering pirfenidone therapy to a patient in need thereof, comprising discontinuing pirfenidone during the time period of ciprofloxacin use at a dose of 750 mg or higher, or at a dose of between about 650 mg to about 850 mg, or between about 700 mg to about 800 mg, e.g. at doses of 750 mg taken twice a day. For example, in such embodiments, pirfenidone is discontinued before a time period during which ciprofloxacin is administered to the patient, and pirfenidone is restarted after the time period. Discontinuing and/or restarting can occur within, e.g. one day or one week of the time period of concomitant ciprofloxacin use. The time period of ciprofloxacin use can be any appropriate time period, e.g. one week, two weeks, three weeks, or one month. In related embodiments, pirfenidone is discontinued during concomitant administration of ciprofloxacin at equivalent doses by other routes.

The present disclosure is also based in part on the discovery of a novel therapeutic dose of pirfenidone for treatment of patients receiving co-administration of ciprofloxacin.

In a second aspect, the disclosure provides an improved method of administering pirfenidone therapy to a patient in need thereof, comprising reducing the dose of pirfenidone administered to the patient, e.g., by about one-half to about one-third, during concomitant use of ciprofloxacin at a dose of 750 mg, or at a dose of between about 650 mg to about 850 mg, or between about 700 mg to about 800 mg, e.g. at doses of 750 mg twice per day. For example, if a patient has been receiving about 2400 or 2403 mg/day pirfenidone (e.g., given as 801 mg three times per day) prior to ciprofloxacin administration, then such methods include (a) administering pirfenidone at about 1600 or 1602 mg/day (e.g., given as 534 mg three times per day) and (b) concomitantly administering ciprofloxacin at 750 mg twice per day (i.e. 1500 mg/day). In specific embodiments, where the pirfenidone unit dosage form is a 267 mg capsule, and pirfenidone has been administered as three capsules three times per day, then in step (a) each dose of pirfenidone is reduced to two capsules, three times per day. As another example, if a patient has been receiving 1800 mg/day pirfenidone (e.g., given as 600 mg three times per day), then such methods include (a) administering pirfenidone at 1200 mg/day (e.g., given as 400 mg three times per day), and (b) concomitantly administering ciprofloxacin at 750 mg twice per day.

The disclosure also provides use of pirfenidone at a total daily dose that is reduced e.g., by about one-half to about one-third, during concomitant use of ciprofloxacin at a dose of between about 650 mg to about 850 mg, or between about 700 mg to about 800 mg, e.g. at a dose of 750 mg twice per day. The invention further contemplates such use of pirfenidone in one or more unit dosage forms. In specific embodiments, where the pirfenidone unit dosage form is a 267 mg capsule, the invention provides use of pirfenidone at a total daily dose of 1602 mg in two unit dosage units three times a day in a patient concurrently receiving 750 mg ciprofloxacin twice per day. The invention therefore also contemplates a pharmaceutical composition comprising pharmaceutically acceptable excipients and 1602 mg/day pirfenidone in one or more unit dosage forms for such use.

Pharmaceutically acceptable excipients refer to substances such as disintegrators, binders, fillers, and lubricants used in formulating pharmaceutical products which are not active pharmaceutical ingredients, as would be well known to those skilled in the art. In embodiments of the pharmaceutical composition of the present invention, the dosage unit may be a capsule, including a capsule containing 267 mg pirfenidone and pharmaceutically acceptable excipients In related embodiments, the present disclosure involves reduced dosage of pirfenidone, during concomitant ciprofloxacin administration, when the drug(s) are given at equivalent doses by other routes. Intravenous (i.v.) dosing of ciprofloxacin 400 mg i.v. three times per day (every 8 hours) is considered the equivalent of 750 mg orally twice per day.

As used herein, "concomitant use" is understood to be interchangeable with concurrent administration or co-administration. Thus, the terms are understood to encompass administration simultaneously, or at different times, and by the same route or by different routes, as long as the two agents are given in a manner that allows both agents to be affecting the body at the same time. For example, concomitant use can refer to a medication concomitantly administered, whether prescribed by the same or a different practitioner, or for the same or a different indication. With respect to routes of administration, a preferred route of administration by the disclosure is oral administration. Additionally, the drugs may be delivered to a patient using any standard route of administration, including parenterally, such as intravenously, intraperitoneally, intrapulmonary, subcutaneously or intramuscularly, intrathecally, transdermally, rectally, orally, nasally or by inhalation.

In any of the aspects or embodiments, the patient may have idiopathic pulmonary fibrosis (IPF), bronchiolitis obliterans (BO), renal fibrosis or scleroderma and the medicament, use or administration is for treatment of these fibrotic disorders. In any of the aspects or embodiments, the therapeutically effective amount of pirfenidone being administered prior to the need for ciprofloxacin therapy may be a daily dosage of about 2400 mg per day, e.g. 2403 mg per day. In any of the aspects of the disclosure, the daily dosage may be administered in divided doses three times a day, or two times a day, or alternatively is administered in a single dose once a day. In any of the aspects of the disclosure, the pirfenidone may be administered with food. For example, a daily oral dosage of 2400 mg or 2403 mg pirfenidone per day may be administered as follows: 800 mg or 801 mg taken three times a day, with food. Similarly, a daily oral dosage of 1600 mg or 1602 mg pirfenidone per day may be administered as 534 mg taken three times a day, with food. In any of the embodiments, the pirfenidone may be administered in oral unit dosage forms, e.g. capsules or tablets. In any of the embodiments, the amount of pirfenidone in the unit dosage form can be 200 mg or 267 mg.

In any of the aspects or embodiments of the disclosure, it is understood that the patient is in need of therapy with ciprofloxacin.

In some embodiments, ciprofloxacin at a dose of 750 mg, e.g. 750 mg twice per day, is used with caution when administering pirfenidone. In further embodiments, ciprofloxacin at a dose of between about 650 mg to about 850 mg or between about 700 mg to about 800 mg, e.g. twice per day, is used with caution when administering pirfenidone.

A further aspect of the disclosure provides the use of pirfenidone in the manufacture of a medicament for treating a patient in need of pirfenidone therapy, characterized in that the treating comprises avoiding co-administration of ciprofloxacin at a dose of 750 mg, e.g. given twice per day, or discontinuing pirfenidone during ciprofloxacin use at a dose of 750 mg, or reducing the dose of pirfenidone (e.g., by about one-third) during ciprofloxacin use at a dose of 750 mg. It is understood that this also applies to ciprofloxacin at a dose of between about 650 mg to about 850 mg or between about 700 mg to about 800 mg.

For simplicity of dosing and improved safety, the invention also contemplates that, for patients concurrently being administered ciprofloxacin (e.g. at any dose, 250 mg, 500 mg or 750 mg given twice daily) and pirfenidone, pirfenidone is administered at a dose of about 1602 mg/day, or about 1600 mg/day, or a dose reduced by about one-third (from a reference dose, e.g., 1800 mg/day or 2403 mg/day).

For simplicity of dosing and improved safety, the invention also contemplates that, for patients concurrently being administered ciprofloxacin (e.g. at any dose, 250 mg, 500 mg or 750 mg given twice daily) and pirfenidone, pirfenidone is administered at a dose of about 801 mg/day, or about 800 mg/day, or a dose reduced by about two-thirds (from a reference dose, e.g., 1800 mg/day or 2403 mg/day).

It is also understood that any of the aspects or embodiments or examples described herein with respect to methods of treatment apply equally to "pirfenidone for use" in such methods and to use of pirfenidone for treatment and in manufacture of a medicament for such methods. Such example uses are also further described below. It is further understood that the methods and uses described herein relating to the concurrent administration of ciprofloxacin and pirfenidone apply equally to ciprofloxacin, as well as pirfenidone. Thus, any of the aspects or embodiments or examples described herein with respect to methods of treatment apply equally to "ciprofloxacin for use" in such methods and to use of ciprofloxacin in manufacture of a medicament for such methods. By way of example, any references to "pirfenidone for use" apply equally to "ciprofloxacin for use."

In any of the aspects or embodiments of the disclosure, the patient is in need of pirfenidone therapy. The effect of ciprofloxacin on increasing pirfenidone exposure applies to any patient receiving pirfenidone therapy, and is independent from the disorder for which the patient is in need of pirfenidone. In this case, the inhibition of CYP1A2 by ciprofloxacin that leads to an increase in exposure to pirfenidone in a patient is not a consequence or a result of a particular disorder. As such, it is contemplated that any disorder for which a patient would be receiving pirfenidone, and during which a patient might be receiving the antibiotic ciprofloxacin for any reason including reasons unrelated to pirfenidone administration, is one that would benefit from the disclosure.

For example, the patient suffers from a fibrotic disorder, such as a fibrotic disorder of the lung, kidney, liver, heart, or other organ; an inflammatory disease; an autoimmune disease; or fibrosis accompanying tissue injury from, e.g., infarction, infection, cancer, cirrhosis, and the like. Pirfenidone is known to possess both anti-fibrotic and anti-inflammatory activities. For example, the patient suffers from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute or chronic renal disease; renal fibrosis; diabetic nephropathy; irritable bowel syndrome; pyresis; restenosis; cerebral malaria; stroke or ischemic injury; neural trauma; Alzheimer's disease; Huntington's disease; Parkinson's disease; acute or chronic pain; allergies, including allergic rhinitis or allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, or non-small cell lung cancer; graft-versus-host reaction; or autoimmune diseases, such as multiple sclerosis, lupus or fibromyalgia; AIDS or other viral diseases such as Herpes Zoster, Herpes Simplex I or II, influenza virus, Severe Acute Respiratory Syndrome (SARS) or cytomegalovirus; or diabetes mellitus, proliferative disorders (including both benign or malignant hyperplasias), acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases; pain disorders including neuromuscular pain, headache, cancer pain, dental pain, or arthritis pain; angiogenic disorders including solid tumor angiogenesis, ocular neovascularization, or infantile hemangioma; conditions associated with the cyclooxygenase or lipoxygenase signaling pathways, including conditions associated with prostaglandin endoperoxide synthase-2 (including edema, fever, analgesia, or pain); organ hypoxia; thrombin-induced platelet aggregation; or protozoal diseases. For example, IPF and scleroderma (or systemic sclerosis) associated interstitial lung disease (SSc-ILD) share overlapping pathologic pathways, most notably the activation and proliferation of fibroblasts, expression of fibrogenic cytokines and growth factors, and progressive interstitial fibrosis (Tzouvelekis et al. 2005; Castro and Jimenez 2010; Collard et al. 2010; Hummers 2010; van den Blink et al. 2010; Richards et al. 2012; Vij and Noth 2012). IPF and SSc-ILD also have biomarkers in common, including CCL 18, SP-A, SP D, KL 6, ICAM-1, VCAM 1, CCL 2, YKL-40, and vWF.

Any of the uses or methods described herein can be carried out for avoiding the potential for reduced clearance of pirfenidone and/or for avoiding the potential for increased exposure to pirfenidone and/or to reduce side effects or toxicity of pirfenidone administration and/or to improve the safety of pirfenidone administration. As detailed in the examples herein, a patient concurrently receiving both pirfenidone and ciprofloxacin at a dose of 750 mg will experience an increased exposure to pirfenidone of about 1.8-fold, due to the reduced clearance of pirfenidone. The uses or methods described herein avoid such increased exposure, thereby reducing dose-dependent side effects or toxicity associated with pirfenidone. For example, reducing a 2403 mg dose by about one-half to about one-third, when concomitantly administering ciprofloxacin at a dose of 750 mg, will result in an effective pirfenidone exposure that is equivalent to a 2403 mg dose when given in the absence of ciprofloxacin. Similarly, reducing a 1800 mg dose by about one-half to about one-third when concomitantly administering ciprofloxacin at a dose of 750 mg, will result in an effective pirfenidone exposure that is equivalent to a 1800 mg dose when given in the absence of ciprofloxacin.

In another aspect, the disclosure provides a package or kit comprising (a) pirfenidone, optionally in a container, and (b) a package insert, package label, instructions or other labeling directing or disclosing any of the methods or embodiments disclosed herein.

BRIEF DESCRIPTION OF THE DRAWING

FIG. 1 depicts the mean (±Standard Deviation (SD)) concentration of pirfenidone and 5-carboxy-pirfenidone versus time since dose of ciprofloxacin.

DETAILED DESCRIPTION OF THE INVENTION

Pirfenidone is an orally active, anti-fibrotic agent. Results of in vitro experiments indicated that pirfenidone is primarily metabolized by CYP1A2 with multiple other CYPs contributing as well (i.e., 1A1, 2A6, 2B6, 2C8, 2C9, 2C18, 2C19, 2D6, 2E1, 2J2, 3A4, 3A5, 4A11, and 4F2) [U.S. Pat. No. 7,816,383, incorporated by reference herein in its entirety]. The data reported herein show that, in vivo, CYP1A2 is responsible for the vast majority of pirfenidone metabolism (70-80%).

Oral administration of pirfenidone results in the formation of four metabolites, 5 hydroxymethyl-pirfenidone, 5 carboxy-pirfenidone, 4'-hydroxy-pirfenidone, and the 5 O-acyl glucuronide metabolite of 5 carboxy-pirfenidone. In humans, only pirfenidone and 5-carboxy-pirfenidone are present in plasma in significant quantities; none of the other metabolites occur in sufficient quantities to allow for PK analysis. There are no unique human metabolites.

Data reported herein show that co-administration of an oral dose of 801 mg pirfenidone with an oral dose of 750 mg ciprofloxacin resulted in an approximate 1.8-fold (~81%) increase in exposure (AUC, or Area Under the Curve) of pirfenidone. Thus, for example, a patient receiving a daily dose of 2403 mg may be exposed to pirfenidone levels equivalent to a dose of about 4325 mg pirfenidone. In contrast, a patient receiving a daily dose that is reduced from 2403 mg by about one-third to about one-half may be exposed to pirfenidone levels equivalent to a dose of about 2403 mg. Computer modeling of the effect of lower doses of ciprofloxacin, e.g. the 500 mg or 250 mg oral doses, suggests less of an effect on pirfenidone levels, e.g. an approximately 1.5-fold or 1.3-fold increase in exposure, respectively.

DEFINITIONS

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

As used herein, a patient "in need of pirfenidone therapy" is a patient who would benefit from administration of pirfenidone. The patient may be suffering from any disease or condition for which pirfenidone therapy may be useful in ameliorating symptoms. Pirfenidone is a known anti-fibrotic agent, so such disorders include fibrotic disorders, such as fibrotic disorders of the lung, kidney, liver, heart, or other organs. Other disorders that would benefit from therapy with pirfenidone include inflammatory disorders or autoimmune disorders. Yet other disorders that would benefit from therapy with pirfenidone include diseases that result in fibrosis, or where accompanying fibrosis is responsible in part for symptoms or complications of the disease, such as infarctions (tissue death), infection, cancer, cirrhosis, and the like. For example, such diseases or conditions include pulmonary fibrosis, idiopathic pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis; diabetic nephropathy; irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as multiple sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases.

As used herein, a patient in need of "ciprofloxacin therapy" is understood to be a patient in need of "antibiotic therapy" or "fluoroquinolone therapy." Such patients include patients suffering from bacterial infections.

For CYP enzymes, the FDA generally defines a "strong inhibitor" as one that caused a >5-fold increase in the plasma AUC values or more than 80% decrease in clearance of CYP substrates (not limited to sensitive CYP substrate) in clinical evaluations. The FDA generally defines a "moderate inhibitor" as one that caused a >2- but <5-fold increase in the AUC values or 50-80% decrease in clearance of sensitive CYP substrates when the inhibitor was given at the highest approved dose and the shortest dosing interval in clinical evaluations.

Avoiding or Discontinuing Administration of Pirfenidone or Ciprofloxacin

As used herein, the term "avoid" and forms thereof are contemplated to have as alternatives the terms abstain, desist, forbear, and refrain, and forms thereof. In some cases, the alternative terms will be equivalent. For example, "avoiding" means "refraining from." *Merriam-Webster Online Dictionary*, 11$^{th}$ ed., 24 Nov. 2009. As used herein, the term "discontinue" and forms thereof are contemplated to have as alternatives the terms cease, stop, suspend, and quit.

The first aspect of the invention relates to avoiding concomitant use of pirfenidone in a patient with ciprofloxacin at a dose equivalent to 750 mg orally, e.g. 750 mg twice per day (1500 mg/day). It is understood that the patient is in need of pirfenidone therapy and in need of antibiotic therapy. In such methods, pirfenidone is avoided during ciprofloxacin administration, or ciprofloxacin is avoided during pirfenidone administration. In related methods, pirfenidone is discontinued during ciprofloxacin administration or ciprofloxacin is discontinued during pirfenidone administration. Due to the typically short-term nature of ciprofloxacin therapy, it will usually be more convenient to discontinue pirfenidone for the time period of ciprofloxacin administration. The pirfenidone dose that is avoided may be any dose, e.g. ranging from about 1000 to about 4000 mg pirfenidone, or about 1800 mg to about 3600 mg pirfenidone, or about 1800 to about 2500 mg pirfenidone, or about 2200 to about 2600 mg pirfenidone.

In embodiments of such methods, the methods avoid concomitant administration of pirfenidone and ciprofloxacin at equivalent doses by other routes. Intravenous (i.v.) dosing of ciprofloxacin 400 mg i.v. three times per day (every 8 hours) is considered the equivalent of 750 mg orally twice per day.

In some embodiments in which pirfenidone is discontinued during concomitant ciprofloxacin administration at a dose of 750 mg, e.g. 750 mg twice per day, pirfenidone is discontinued and/or restarted within 1, 2, 3, 4, 5, or 6 days or 1 week prior to or after the time period of ciprofloxacin use. In various embodiments, the time period of ciprofloxacin use is, e.g., about 1 week, 2 weeks, 3 weeks, 4 weeks, or 1 month.

In one aspect, concomitant administration of ciprofloxacin at a daily dose of 1500 mg per day (750 mg twice per day) should be avoided during pirfenidone therapy due to the potential for reduced clearance of pirfenidone. The ciprofloxacin dose that is avoided may be within a dosage range (for example and without limitation, between about 650 mg to about 850 mg, optionally given twice per day for a total daily dose of about 1300 mg to about 1700 mg, or between about 700 mg to about 800 mg, optionally given twice per day for a total daily dose of about 1400 mg to about 1600 mg). If ciprofloxacin at a dose of 750 mg cannot be avoided, then the total daily dose of pirfenidone should be reduced during concomitant ciprofloxacin administration.

Selecting an Alternative Drug to Administer Concurrently with Pirfenidone Therapy In examples of methods involving avoiding ciprofloxacin at 750 mg, the methods comprise administering a therapeutically effective amount of pirfenidone to the patient, and administering an alternative antibiotic therapy that is not ciprofloxacin and preferably is not a strong inhibitor of CYP1A2. In some examples, the alternative drug is another fluoroquinolone. In some examples, the alternative drug is also not a moderate to strong inhibitor of both CYP1A2 and another CYP selected from the group consisting of CYP2C9, CYP2C19, CYP2D6 and CYP2E1.

In some embodiments, the patient is administered ciprofloxacin at an alternative dosage (i.e., lower than 750 mg). Thus, in various embodiments, the patient is administered ciprofloxacin at a dose that is 250 mg, 300 mg, 350 mg, 400 mg, 450 mg, or 500 mg, optionally wherein said dose is given two times per day (i.e., BID).

Improving Administration of Pirfenidone by Advising or Cautioning Patient

In some aspects, the disclosure provides a method of administering pirfenidone therapy to a patient in need of pirfenidone therapy (e.g., a patient with IPF), involving administering to the patient a therapeutically effective amount of pirfenidone, and advising the patient in any one, two, three or more of the following ways:

(a) advising the patient that ciprofloxacin at a dose of 750 mg (or between about 650 mg to about 850 mg, or between about 700 mg to about 800 mg), optionally wherein said dose is given twice per day, should be avoided or discontinued, (b) advising the patient that co-administration of pirfenidone with ciprofloxacin at a dose of 750 mg (or between about 650 mg to about 850 mg, or between about 700 mg to about 800 mg), optionally wherein said dose is given twice per day, can alter the therapeutic effect or adverse reaction profile of pirfenidone, (c) advising the patient that the dose of pirfenidone should be reduced in patients being treated with ciprofloxacin at a dose of 750 mg (or between about 650 mg to about 850 mg, or between about 700 mg to about 800 mg), optionally wherein said dose is given twice per day, (d) advising the patient that co-administration of pirfenidone and ciprofloxacin at 750 mg resulted in an approximate 1.8-fold increase in exposure to pirfenidone, and/or (e) advising the patient that ciprofloxacin at 750 mg (or between about 650 mg to about 850 mg, or between about 700 mg to about 800 mg), optionally wherein said dose is given twice per day, should be used with caution in patients receiving pirfenidone due to the potential for reduced pirfenidone clearance and/or increased pirfenidone exposure.

Dosing and Dose Modifications

In various embodiments of the methods described herein, a method of administering pirfenidone and ciprofloxacin concurrently is provided wherein the patient is administered ciprofloxacin at a dosage equivalent to 750 mg orally, e.g. 750 mg twice daily or the patient is administered ciprofloxacin within a dosage range of between about 650 mg to about 850 mg, or between about 700 mg to about 800 mg, optionally wherein said dose is given twice daily, and the patient is administered a reduced dosage of pirfenidone, given orally or by other routes (reduced relative to a patient not taking ciprofloxacin, or relative to the previously administered pirfenidone dosage in the patient). Preferably the dosage of pirfenidone is decreased by about one-half to one-third.

Pirfenidone can be dosed at a total amount of about 50 mg to about 4005 mg, or about 1000 to about 4000 mg pirfenidone, or about 1800 mg to about 3600 mg pirfenidone, or about 1800 to about 2500 mg pirfenidone, or about 2200 to about 2600 mg pirfenidone. In some embodiments, the amount of pirfenidone being administered prior to ciprofloxacin administration is 2400 mg/day or 2403 mg/day. The dosage can be divided into two or three doses over the day or given in a single daily dose. In some embodiments, three capsules of pirfenidone, each capsule comprising about 267-mg of pirfenidone, are administered three times per day. Specific amounts of the total daily amount of the therapeutic contemplated for the disclosed methods include about 50 mg, about 100 mg, about 150 mg, about 200 mg, about 250 mg, about 267 mg, about 300 mg, about 350 mg, about 400 mg, about 450 mg, about 500 mg, about 534 mg, about 550 mg, about 600 mg, about 650 mg, about 700 mg, about 750 mg, about 800 mg, about 850 mg, about 900 mg, about 950 mg, about 1000 mg, about 1050 mg, about 1068 mg, about 1100 mg, about 1150 mg, about 1200 mg, about 1250 mg, about 1300 mg, about 1335 mg, about 1350 mg, about 1400 mg, about 1450 mg, about 1500 mg, about 1550 mg, about 1600 mg, about 1602 mg, about 1650 mg, about 1700 mg, about 1750 mg, about 1800 mg, about 1850 mg, about 1869 mg, about 1900 mg, about 1950 mg, about 2000 mg, about 2050 mg, about 2100 mg, about 2136 mg, about 2150 mg, about 2200 mg, about 2250 mg, about 2300 mg, about 2350 mg, about 2400 mg and about 2403 mg. A reduction of one-third to one-half can be readily calculated.

Dosages of pirfenidone can alternately be administered as a dose measured in mg/kg. Contemplated mg/kg doses of the disclosed therapeutics include about 1 mg/kg to about 40 mg/kg. Specific ranges of doses in mg/kg include about 1 mg/kg to about 30 mg/kg, about 5 mg/kg to about 30 mg/kg, about 10 mg/kg to about 40 mg/kg, about 10 mg/kg to about 30 mg/kg, and about 15 mg/kg to about 35 mg/kg. A reduction of one-third to one-half can be readily calculated.

In one embodiment, a dosage amount of pirfenidone is taken with food. In another embodiment, the patient is instructed to administer the dosage of pirfenidone with food.

In some embodiments, the dose is reduced by about one-half to one-third (e.g. 50% to 67%). In specific embodiments, the dose is reduced by about ⅓ relative to the previously administered dose. In further embodiments, the dose is reduced by about 40%, 50%, 60%, 70% or more relative to the previously administered dose, or to a dose ranging from about 40% to about 70%, or about 50% to about 70% of the previously administered dose.

For example, when the patient has been receiving about 2403 mg/day pirfenidone, the pirfenidone dose is reduced to a range of about 1200 mg/day to about 1700 mg/day, or a range of about 1400 mg/day to about 1650 mg/day, during concomitant ciprofloxacin use.

As another example, when the patient has been receiving about 1800 mg/day pirfenidone, the pirfenidone dose is reduced to a range of about 900 mg/day to about 1300 mg/day, or a range of about 1000 mg/day to about 1250 mg/day, during concomitant ciprofloxacin use.

It is understood that, in such embodiments involving dose reduction, upon discontinuation of ciprofloxacin at a dose of 750 mg or higher (or between about 650 mg to about 850 mg, or between about 700 mg to about 800 mg), e.g. twice daily, the dosage of pirfenidone is titrated back up to the maximum recommended dose for the patient. In some embodiments, the dose of pirfenidone is titrated back up to a dose that is not less than 2400 or 2403 mg/day.

As noted above, in any of the embodiments described herein, including but not limited to discontinuation or dose reduction, the packages and kits, and/or the methods of preparing or packaging pirfenidone, the pirfenidone, uses, methods, packages, kits, advice, warnings, discontinuation or dose titration may apply not only to the oral dose of 750 mg ciprofloxacin, e.g. given twice daily, but also to any other equivalent dose given by another route. Intravenous (i.v.) dosing of ciprofloxacin 400 mg i.v. three times per day (every 8 hours) is considered the equivalent of 750 mg orally twice per day.

Packages, Kits, Methods of Packaging, and Methods of Delivering

In another aspect, a package or kit is provided comprising pirfenidone, optionally in a container, and a package insert, package label, instructions or other labeling including instructions or directions for any of the methods disclosed herein.

The package insert, package label, instructions or other labeling may further comprise directions for treating a patient in need of pirfenidone, e.g. with IPF or any other disorder or disease disclosed herein by administering pirfenidone, e.g., at a dosage of 2400 mg or 2403 mg per day.

In a related aspect, the disclosure provides a method of preparing or packaging a pirfenidone medicament comprising packaging pirfenidone, optionally in a container, together with a package insert or package label or instructions for any of the methods disclosed herein.

In some embodiments, a method of treating a patient in need of pirfenidone is disclosed comprising providing, selling or delivering any of the kits of disclosed herein to a hospital, physician or patient.

In some embodiments, a method of treating a patient in need of ciprofloxacin at 750 mg is provided comprising providing or delivering a kit comprising ciprofloxacin together with a package insert or package label or instructions for any of the methods disclosed herein, to a hospital, physician or patient.

The disclosure will be more fully understood by reference to the following examples which detail exemplary embodiments of the disclosure. They should not, however, be construed as limiting the scope of the disclosure. All citations throughout the disclosure are hereby expressly incorporated by reference.

Examples of Aspects and Embodiments of the Invention

1. Pirfenidone for use in treating a patient in need of pirfenidone therapy wherein the dosage of pirfenidone for administration to a patient is reduced by about one-half to about one-third, preferably one-third, during concomitant administration of ciprofloxacin at an oral dose of 750 mg, or at an oral dose of from 650 mg to 850 mg, or at an oral dose of from 700 mg to 800 mg, for example, 750 mg twice daily (1500 mg/day), or at an intravenous (i.v.) dose of 400 mg i.v. three times per day.

2a. Pirfenidone for use in treating a patient in need of pirfenidone therapy wherein the pirfenidone is for administering to the patient at a therapeutically effective amount, and avoiding concomitant administration of ciprofloxacin at an oral dose of 700 mg or higher, or at an oral dose of 750 mg or higher, for example, an oral dose of 750 mg or higher twice daily (1500 mg or higher per day), or at an intravenous (i.v.) dose of 400 mg or higher i.v. three times per day.

2b. Pirfenidone for use in treating a patient in need of pirfenidone therapy wherein the administration of pirfenidone comprises a time period during which pirfenidone is avoided while ciprofloxacin is administered at an oral dose of 700 mg or higher, or at an oral dose of 750 mg or higher, for example, an oral dose of 750 mg or higher twice daily (1500 mg or higher per day), or at an intravenous dose of 400 mg or higher i.v. three times per day. It is understood that according to this aspect, once ciprofloxacin is discontinued, pirfenidone is restarted.

3. The pirfenidone for use of embodiment 1 wherein the pirfenidone dosage is reduced from about 2403 mg/day to a dosage ranging from about 1400 mg/day to about 1650 mg/day, optionally 1602 mg/day, during ciprofloxacin administration.

4. The pirfenidone for use of embodiment 1 wherein the pirfenidone dosage is reduced from about 1800 mg/day to a dosage ranging from about 1000 mg/day to about 1250 mg/day, optionally 1200 mg/day, during ciprofloxacin administration.

5. The pirfenidone for use of any of embodiments 1-4 wherein the pirfenidone for use is for avoiding the potential for a reduced clearance of pirfenidone or the potential for an increased exposure to pirfenidone.

6. The pirfenidone for use of any one of embodiments 1-5 wherein the total daily dose of pirfenidone is administered to the patient in divided doses three times per day, with food.

7. The pirfenidone for use of any of embodiments 1-6 wherein the pirfenidone is administered in unit dosage forms that are capsules or tablets.

8. The pirfenidone for use of embodiment 7 wherein the amount of pirfenidone in the unit dosage form is 200 mg or 267 mg.

9. The pirfenidone for use of embodiment 3 wherein during concomitant ciprofloxacin administration 534 mg of pirfenidone is administered to the patient three times per day, with food.

10. The pirfenidone for use of embodiment 3 wherein during concomitant ciprofloxacin administration the pirfenidone is administered at a total daily dosage of 1602 mg.

11. The pirfenidone for use of embodiment 3 wherein during concomitant ciprofloxacin administration the pirfenidone is administered at a total daily dosage of about 1600 mg.

12. The pirfenidone for use of any one of embodiments 1-11 wherein the patient has idiopathic pulmonary fibrosis (IPF).

13. The pirfenidone for use of any of embodiments 1-11 wherein the patient has a fibrotic disorder, inflammatory disorder, or autoimmune disorder.

14. The pirfenidone for use of any of embodiments 1-11 wherein the patient suffers from a disease selected from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute or chronic renal disease; renal fibrosis; diabetic nephropathy; irritable bowel syndrome; pyresis; restenosis; cerebral malaria; stroke or ischemic injury; neural trauma; Alzheimer's disease; Huntington's disease; Parkinson's disease; acute or chronic pain; allergies, including allergic rhinitis or allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, or non-small cell lung cancer; graft-versus-host reaction; or autoimmune diseases, such as multiple sclerosis, lupus or fibromyalgia; AIDS or other viral diseases such as Herpes Zoster, Herpes Simplex I or II, influenza virus, Severe Acute Respiratory Syndrome (SARS) or cytomegalovirus; or diabetes mellitus, proliferative disorders (including both benign or malignant hyperplasias), acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases; pain disorders including neuromuscular pain, headache, cancer pain, dental pain, or arthritis pain; angiogenic disorders including solid tumor angiogenesis, ocular neovascularization, or infantile hemangioma; conditions associated with the cyclooxygenase or lipoxygenase signaling pathways, including conditions associated with prostaglandin endoperoxide synthase-2 (including edema, fever, analgesia, or pain); organ hypoxia; thrombin-induced platelet aggregation; or protozoal diseases.

15. Ciprofloxacin for use in treating a patient in need of ciprofloxacin therapy, for example, with a bacterial infection, wherein the dosage of ciprofloxacin is an oral dose of 750 mg, or an oral dose of from 650 mg to 850 mg, or an oral dose of from 700 mg to 800 mg, for example, 750 mg twice daily (1500 mg/day), or an intravenous (i.v.) dose of 400 mg i.v. three times per day, during concomitant administration of pirfenidone, wherein the dosage of pirfenidone for administration to the patient is reduced by about one-half to about one-third, preferably one-third.

16. Ciprofloxacin for use in treating a patient in need of ciprofloxacin therapy wherein the ciprofloxacin is for administration at an oral dose of 700 mg or higher, or at an oral dose of 750 mg or higher, for example, an oral dose of 750 mg or higher twice daily (1500 mg or higher per day), or at an intravenous (i.v.) dose of 400 mg or higher i.v. three times per day, wherein (a) pirfenidone is avoided during concomitant administration of ciprofloxacin, or (b) ciprofloxacin is avoided during concomitant administration of pirfenidone.

17. Ciprofloxacin for use in treating a patient in need of ciprofloxacin therapy wherein the administration of ciprofloxacin occurs during a time period in which pirfenidone is avoided while ciprofloxacin is administered at an oral dose of 700 mg or higher, or at an oral dose of 750 mg or higher, for example, an oral dose of 750 mg or higher twice daily (1500 mg or higher per day), or at an intravenous dose of 400 mg or higher i.v. three times per day. It is understood that according to this aspect, once ciprofloxacin is discontinued, pirfenidone is restarted.

18. The ciprofloxacin for use of embodiment 15 wherein the pirfenidone dosage is reduced from about 2403 mg/day to a dosage ranging from about 1400 mg/day to about 1650 mg/day, optionally 1602 mg/day, during ciprofloxacin administration.

19. The ciprofloxacin for use of embodiment 15 wherein the pirfenidone dosage is reduced from about 1800 mg/day to a dosage ranging from about 1000 mg/day to about 1250 mg/day, optionally 1200 mg/day, during ciprofloxacin administration.

20. The ciprofloxacin for use of any of embodiments 16-17 wherein the pirfenidone is avoided to avoid the potential for a reduced clearance of pirfenidone or the potential for an increased exposure to pirfenidone.

21. The ciprofloxacin for use of embodiment 15 wherein during concomitant ciprofloxacin administration 534 mg of pirfenidone is administered to the patient three times per day, with food.

22. The ciprofloxacin for use of embodiment 15 wherein during concomitant ciprofloxacin administration the pirfenidone is administered at a total daily dosage of 1602 mg.

23. The ciprofloxacin for use of embodiment 15 wherein during concomitant ciprofloxacin administration the pirfenidone is administered at a total daily dosage of about 1600 mg.

24. The ciprofloxacin for use of any one of embodiments 15-23 wherein the patient has idiopathic pulmonary fibrosis (IPF).

25. The ciprofloxacin for use of any of embodiments 15-23 wherein the patient has a fibrotic disorder, inflammatory disorder, or autoimmune disorder.

26. The ciprofloxacin for use of any of embodiments 15-23 wherein the patient suffers from a disease selected from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute or chronic renal disease; renal fibrosis; diabetic nephropathy; irritable bowel syndrome; pyresis; restenosis; cerebral malaria; stroke or ischemic injury; neural trauma; Alzheimer's disease; Huntington's disease; Parkinson's disease; acute or chronic pain; allergies, including allergic rhinitis or allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, or non-small cell lung cancer; graft-versus-host reaction; or autoimmune diseases, such as multiple sclerosis, lupus or fibromyalgia; AIDS or other viral diseases such as Herpes Zoster, Herpes Simplex I or II, influenza virus, Severe Acute Respiratory Syndrome (SARS) or cytomegalovirus; or diabetes mellitus, proliferative disorders (including both benign or malignant hyperplasias), acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases; pain disorders including neuromuscular pain, headache, cancer pain, dental pain, or arthritis pain; angiogenic disorders including solid tumor angiogenesis, ocular neovascularization, or infantile hemangioma; conditions associated with the cyclooxygenase or lipoxygenase signaling pathways, including conditions associated with prostaglandin endoperoxide synthase-2 (including edema, fever, analgesia, or pain); organ hypoxia; thrombin-induced platelet aggregation; or protozoal diseases.

27. Use of pirfenidone at a total daily dose that is reduced by about one-half to about one-third, during concomitant use of ciprofloxacin at a dose of between about 650 mg to about 850 mg twice daily.

28. Pirfenidone for use at a total daily dose that is reduced, by about one-half to about one-third, during concomitant use of ciprofloxacin at a dose of between about 650 mg to about 850 mg twice daily.

29. The use of embodiment 27, or the pirfenidone for use of embodiment 28, where the concomitant use of ciprofloxacin is at a dose of between about 700 mg to about 800 mg twice daily.

30. The use of embodiment 27, or the pirfenidone for use of embodiment 28, where the concomitant use of ciprofloxacin is at a dose of 750 mg twice daily (1500 mg/day).

31. The use or pirfenidone for use of any one of embodiments 27-30 wherein the total daily dose of pirfenidone is reduced from about 2403 mg/day to between about 1400 mg/day to about 1650 mg/day.

32. The use or pirfenidone for use of any one of embodiments 27-30 wherein the total daily dose of pirfenidone is reduced from about 2403 mg/day to about 1602 mg/day.

33. The use or pirfenidone for use of any one of embodiments 27-30 wherein the total daily dose of pirfenidone is reduced from about 1800 mg/day to between about 1000 mg/day to about 1250 mg/day.

34. The use or pirfenidone for use of any one of embodiments 27-30 wherein the total daily dose of pirfenidone is reduced from about 1800 mg/day to about 1200 mg/day.

35. The use or pirfenidone for use of any of embodiments 27-34 for avoiding potential for a reduced clearance of pirfenidone or potential for an increased exposure to pirfenidone.

36. The use or pirfenidone for use of any one of embodiments 27-35 wherein the total daily dose of pirfenidone is for administration in divided doses three times per day, with food.

37. The use or pirfenidone for use of any of embodiments 27-36 wherein the pirfenidone is in one or more unit dosage forms that are capsules or tablets.

38. The use or pirfenidone for use of embodiment 37 wherein the amount of pirfenidone in each of the one or more unit dosage forms is 200 mg or 267 mg.

39. The use or pirfenidone for use of embodiment 37 wherein the pirfenidone is in a 267 mg capsule.

40. The use or pirfenidone for use of any one of embodiments 27-32, 35-39, wherein the amount of pirfenidone is 534 mg, in two unit dosage forms for administration three times per day, with food.

41. The use or pirfenidone for use of any one of embodiments 27-31, 35-40, wherein the total daily dose of pirfenidone is reduced to 1602 mg/day.

42. The use or pirfenidone for use of any one of embodiments 27-31, 35-40, wherein the total daily dose of pirfenidone is reduced to about 1600 mg/day.

43. The use or pirfenidone for use of any one of embodiments 27-42 in a patient that has idiopathic pulmonary fibrosis (IPF).

44. The use or pirfenidone for use of any of embodiments 27-42 in a patient that has a fibrotic disorder, inflammatory disorder, or autoimmune disorder.

45. The use or pirfenidone for use of any of embodiments 27-42 in a patient that suffers from a disease selected from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonehritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute or chronic renal disease; renal fibrosis; diabetic nephropathy; irritable bowel syndrome; pyresis; restenosis; cerebral malaria; stroke or ischemic injury; neural trauma; Alzheimer's disease; Huntington's disease; Parkinson's disease; acute or chronic pain; allergies, including allergic rhinitis or allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis, tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, or non-small cell lung cancer; graft-versus-host reaction; or autoimmune diseases, such as multiple sclerosis, lupus or fibromyalgia; AIDS or other viral diseases such as Herpes Zoster, Herpes Simplex I or II, influenza virus, Severe Acute Respiratory Syndrome (SARS) or cytomegalovirus; or diabetes mellitus, proliferative disorders (including both benign or malignant hyperplasias), acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases; pain disorders including neuromuscular pain, headache, cancer pain, dental pain, or arthritis pain; angiogenic disorders including solid tumor angiogenesis, ocular neovascularization, or infantile hemangioma; conditions associated with the cyclooxygenase or lipoxygenase signaling pathways, including conditions associated with prostaglandin endoperoxide synthase-2 (including edema, fever, analgesia, or pain); organ hypoxia; thrombin-induced platelet aggregation; or protozoal diseases.

46. Use of pirfenidone at a total daily dose of 1602 mg/day, for the treatment of a fibrotic disorder in a patient concomitantly receiving ciprofloxacin at a dose of 750 mg three times daily.

47. Pirfenidone for use at a total daily dose of 1602 mg/day for the treatment of a fibrotic disorder in a patient concomitantly receiving ciprofloxacin at a dose of 750 mg three times daily 48. Use of pirfenidone or pirfenidone for use according to embodiments 46 and 47 adapted for administration in one or more unit dosage forms three times daily.

49. Use of pirfenidone or pirfenidone for use according to embodiment 48 wherein the unit dosage form is 267 mg capsule.

50. Use of pirfenidone or pirfenidone for use according to any of embodiments 46-49 wherein the fibrotic disorder is selected from the group consisting of idiopathic pulmonary fibrosis (IPF), bronchiolitis obliterans (BO), renal fibrosis and scleroderma.

51. A pharmaceutical composition comprising a pharmaceutically acceptable excipient and 1602 mg pirfenidone in one or more unit dosage forms for use to treat a fibrotic disorder in a patient concomitantly receiving ciprofloxacin at a dose of 750 mg twice daily.

52. The pharmaceutical composition according to embodiment 51 wherein the fibrotic disorder is selected from the group consisting of idiopathic pulmonary fibrosis (IPF), bronchiolitis obliterans (BO), renal fibrosis and scleroderma.

53. A package or kit comprising (a) pirfenidone, optionally in a container, and (b) a package insert, package label, instructions or other labeling for the use or pirfenidone for use according to any of embodiments 27-52.

EXAMPLES

Example 1

An Open-Label Phase 1 Study to Determine the Impact of Ciprofloxacin on the Pharmacokinetics and Safety of Pirfenidone A Phase 1, open-label crossover study was carried out to investigate the impact of ciprofloxacin administration on the pharmacokinetics and safety of pirfenidone. The study enrolled 27 healthy subjects. Subjects were enrolled at one Phase 1 clinical center and were screened up to 28 days before dosing. After meeting inclusion/exclusion criteria, subjects were admitted to the clinic on Day −1 in preparation for dosing with a single 801 mg dose of pirfenidone with food on Day 1. Subjects had blood and urine samples collected for pharmacokinetic (PK) analysis of pirfenidone and its major metabolite, 5-carboxy-pirfenidone, before dosing (blood PK only) and at various times during the 32 hours (h) after the pirfenidone dose. Subjects were discharged from the clinic on Day 2 after safety assessments and the final PK sample collection. On Days 2 through 7, subjects received ciprofloxacin, a moderate CYP1A2 inhibitor (self-administered while outside the clinic). On Days 2 through 6, subjects completed diary cards, on which they recorded ciprofloxacin dosing and any adverse events (AEs) experienced. On Day 5, subjects were readmitted to the clinic. On Day 6, each subject received a single 801-mg dose of pirfenidone in addition to the ciprofloxacin. Blood and urine samples were collected for pirfenidone and 5-carboxy-pirfenidone PK analysis, using the same sampling schedule as on Day 1. All subjects were discharged on Day 7 after safety assessments and the final PK sample collection. A follow-up telephone call occurred approximately 24 h after subjects were discharged from the clinic (Day 8).

Ciprofloxacin inhibits CYP1A2 activity [Karjalainen et al., Basic and Clinical Pharmacology & Toxicology 103: 157-165 (2008)]. The selected dose of ciprofloxacin (750 mg twice daily [BID]) is higher than the typical prescribed doses of 250-500 mg BID and was chosen to maximize the CYP1A2 inhibition effects of this drug. The duration of ciprofloxacin administration, before concurrent administration of pirfenidone and subsequent PK sampling, was 4 days. Given the short half-life of ciprofloxacin (approximately 3-5 hours), steady-state would be achieved well within the 4 days of dosing.

Inclusion criteria included the following:
18 to 55 years old (inclusive) at the time of consent
Body mass index (BMI) of 18 kg/m² to 40 kg/m² (inclusive)
No pregnancy
Abstaining from alcohol from 48 h before dosing through the final study visit.
In good health as indicated by medical history, physical examination, vital signs, electrocardiogram (ECG), and clinical laboratory assessments.

Exclusion criteria included the following:
History of or active cardiovascular, respiratory, hepatic, renal, gastrointestinal, endocrine, or neurological disorders capable of altering the absorption, metabolism, or elimination of drugs
History of clinically significant illness within 30 days before the first dose of study drug
Previous adverse event (AE), allergic reaction, or sensitivity to ciprofloxacin
Consumption of grapefruit, grapefruit juice, or any fruit juice within 48 h before the first dose of study drug
Use of products containing alcohol, caffeine, or xanthine within 48 h before dosing
Consumption of cruciferous vegetables (i.e., broccoli, brussels sprouts, kale, etc.) or chargrilled meat within 48 h before dosing
Use of tobacco products within 3 months of first dose of study drug
Use of concomitant medications (including non-prescription drugs)

Dosing

Pirfenidone
801 mg (given as 3×267-mg capsules) orally with food in the morning on Days 1 and 6.
Ciprofloxacin
750-mg tablets orally, as follows:
Day 2: 750 mg in the evening
Days 3-6: 750 mg twice a day (BID)
Day 7: 750 mg in the morning.
The 750 mg BID dose of ciprofloxacin was chosen as the most likely to result in a moderate and relatively selective inhibition of CYP1A2 activity [Karjalainen et al., Basic and Clinical Pharmacology & Toxicology 103: 157-165 (2008)]. This dose is approved for use in severe infections but is higher than the more commonly prescribed dose of 500 mg BID, thereby providing a "worst-case" scenario for selective, moderate CYP1A2 inhibition.
Duration of Treatment:
Pirfenidone on Days 1 and 6; ciprofloxacin on Days 2 through 7

Statistical Methods

Pharmacokinetics:
The PK population was defined as subjects who received both doses of pirfenidone (Days 1 and 6), had at least 4 plasma PK samples, were at least 80% compliant with ciprofloxacin dosing on Days 2, 3, and 4 (i.e., administered at least 3000 mg of the protocol-mandated doses), and who had administered the entire amount of all doses of ciprofloxacin on Days 5, 6, and 7 (3750 mg total).

Both noncompartmental methods and a previously derived population PK (i.e., compartmental) model were used to analyze the plasma concentration-time data and characterize individual subject PK parameters. Effects of ciprofloxacin coadministration on pirfenidone and its primary metabolite, 5-carboxy pirfenidone, $AUC_{0-\infty}$ and $C_{max}$ were tested using accepted criteria for bioequivalence for paired data.
Safety:
The Safety population was defined as subjects who received any amount of pirfenidone or ciprofloxacin.

Results

Baseline Subject Characteristics:
The study group consisted of 17 males and 10 females, ranging in age from 18 to 49 years (median 24 years). The study group was predominantly white (21 subjects, 77.8%) with 2 subjects (7.4%) each of American Indian/Alaska Native, Asian, and black/African-American race. BMI ranged from 18.6 to 32.6 kg/m² (median 24.4 kg/m²). Medical histories were generally unremarkable, and no subjects were receiving any concomitant medications at Baseline.
Pharmacokinetic Results:
For pirfenidone with coadministration of ciprofloxacin, the differences in $C_{max}$ and $T_{max}$ (time to peak plasma concentration) were modest between Day 1/2 and Day 6/7; the geometric mean C max was approximately 20% higher on Day 6/7 while median $T_{max}$ was the same on both occasions (2 h). The apparent terminal elimination half-life for pirfenidone was slightly prolonged on Day 6/7, but remained relatively short (geometric mean of 4.1 h vs. 2.4 h on Day 1/2). The most pronounced effect of ciprofloxacin coadministration on pirfenidone was seen with $AUC_{0-\infty}$, which was approximately 78% higher with coadministration of ciprofloxacin on Day 6/7 compared with Day 1/2.

For 5-carboxy-pirfenidone, the differences in $C_{max}$ and $T_{max}$ were also modest when comparing Day 1/2 with Day 6/7; the trend for $C_{max}$ was reversed (40% lower with ciprofloxacin coadministration on Day 6/7), and the median $T_{max}$ estimates were again identical. The trends in apparent terminal elimination half-life were similar to those seen for pirfenidone; slightly prolonged on Day 6/7, but remaining relatively short (geometric mean of 4.0 h vs. 2.6 h on Day 1/2). The effect of ciprofloxacin coadministration on 5-carboxy-pirfenidone $AUC_{0-\infty}$ was less pronounced; the Day 6/7 geometric mean was only 7.7% lower than that on Day 1/2.

Based on bioequivalence criteria, the coadministration of ciprofloxacin with pirfenidone causes a statistically significant increase in $AUC_{0-\infty}$ (geometric mean ratio [GMR][90% confidence interval (CI)] of 1.81 [1.70-1.93]). The magnitude of the effect (<2-fold increase in exposure) indicates that ciprofloxacin would be classified as a mild inhibitor of pirfenidone clearance at the administered dose of 750 mg (EMEA 2010; US FDA 2006). The effect on pirfenidone $C_{max}$ was more modest but still statistically significant (GMR [90% CI] of 1.23 [1.14-1.31]). There was not a statistically significant effect of ciprofloxacin coadministration on 5-carboxy-pirfenidone $AUC_{0-\infty}$ (GMR [90% CI] of 0.96 [0.92-1.00]). However, the delay in pirfenidone clearance resulted in a statistically significant decrease in the 5-carboxy-pirfenidone $C_{max}$ (GMR [90% CI] of 0.62 [0.57-0.66]).

Safety Results:

Twenty-five treatment-emergent adverse events (TEAEs) were reported for 9 subjects (33.3%). For most of these 9 subjects, the greatest severity of AE was mild (7 subjects, 25.9%); while for 2 subjects (7.4%), the most severe AE reported was moderate. Both moderate AEs were considered not related to either study drug.

For 6 subjects, the strongest pirfenidone relationship for AEs, as assessed by the investigator, was probably related to pirfenidone. One subject experienced AEs considered related to pirfenidone on Day 1 (dosing with pirfenidone only); the remaining 5 subjects experienced AEs only on Day 6 (coadministration with ciprofloxacin

CONCLUSIONS

A statistically significant increase in both $AUC_{0-\infty}$ and $C_{max}$ of pirfenidone was observed with administration of ciprofloxacin 750 mg BID (a high dose of a moderate and relatively selective CYP1A2 inhibitor) for 5 days. However, the magnitude of the effect was relatively modest: An 81% increase (i.e., <2-fold) for $AUC_{0-\infty}$ and a 23% increase in pirfenidone $C_{max}$ were observed with coadministration of ciprofloxacin (see FIG. 1).

TABLE 1

Summary statistics for plasma pharmacokinetic parameters, stratified by study day (N = 27).

| Study Day | Statistic | $C_{max}$ (μg/mL) | $T_{max}$ (h) | $T_{1/2}$ (h) | $AUC_{0-\infty}$ (μg*hr/mL) |
|---|---|---|---|---|---|
| Pirfenidone | | | | | |
| 1/2 (Pre-Ciprofloxacin) | Mean (SD) | 10.4 (2.14) | 2.2 (0.64) | 2.5 (0.6) | 51.9 (14) |
| | % CV | 20.5 | 28.8 | 23.8 | 27 |
| | Median | 10.4 | 2 | 2.4 | 53.2 |
| | Min, Max | 6.6, 14.4 | 1, 3 | 1.4, 3.6 | 30, 88.2 |
| | Geometric Mean | 10.7 | 2.2 | 2.4 | 50.8 |
| | Geometric % CV | 23.9 | 35.2 | 32.2 | 30.5 |
| 6/7 (During Ciprofloxacin) | Mean (SD) | 12.7 (2.17) | 2.6 (0.85) | 4 (0.7) | 93.2 (20) |
| | % CV | 17.1 | 33.3 | 17.5 | 21.5 |
| | Median | 12.8 | 2 | 4 | 95.2 |
| | Min, Max | 7.3, 16.3 | 1, 4.1 | 2.8, 5.6 | 47.1, 126.6 |
| | Geometric Mean | 13 | 2.3 | 4.1 | 90.3 |
| | Geometric % CV | 18.5 | 39.8 | 19.1 | 24.5 |
| 5-Carboxy-Pirfenidone | | | | | |
| 1/2 (Pre-Ciprofloxacin) | Mean (SD) | 6.1 (1.44) | 2.3 (0.6) | 2.7 (0.73) | 30.9 (4.74) |
| | % CV | 23.4 | 26.3 | 27.1 | 15.3 |
| | Median | 5.7 | 2 | 2.6 | 30.3 |
| | Min, Max | 4.4, 9.4 | 1, 3 | 1.4, 4.6 | 22.4, 42.9 |
| | Geometric Mean | 6.5 | 2.2 | 2.6 | 32.6 |
| | Geometric % CV | 27.4 | 35.2 | 39.2 | 16.8 |
| 6/7 (During Ciprofloxacin) | Mean (SD) | 3.8 (0.8) | 2 (0.76) | 4.2 (0.93) | 29.6 (4.52) |
| | % CV | 21.1 | 38.6 | 22.3 | 15.3 |
| | Median | 3.8 | 2 | 4 | 29.1 |
| | Min, Max | 2.6, 5.4 | 1, 4 | 2.6, 6.1 | 19.7, 39.4 |
| | Geometric Mean | 3.8 | 2.1 | 4 | 30.1 |
| | Geometric % CV | 23.6 | 48.6 | 23.5 | 16.9 |

$C_{max}$ = peak plasma concentration
$T_{max}$ = time to maximum plasma concentration
$T_{1/2}$ = apparent terminal elimination half-life
$AUC_{0-\infty}$ = area under the plasma concentration versus time curve from time zero to infinity

TABLE 2

Effect of ciprofloxacin coadministration on pirfenidone (N = 27).

| Analyte/Parameter | Geometric Mean Ratio[a] (90% Confidence Interval)[b] |
|---|---|
| Pirfenidone | |
| $AUC_{0-\infty}$ | 1.81 (1.70, 1.93) |
| $C_{max}$ | 1.23 (1.14, 1.31) |

TABLE 2-continued

Effect of ciprofloxacin coadministration on pirfenidone (N = 27).

| Analyte/Parameter | Geometric Mean Ratio[a] (90% Confidence Interval)[b] |
|---|---|
| 5-Carboxy-Pirfenidone | |
| $AUC_{0-\infty}$ | 0.96 (0.92, 1.00) |
| $C_{max}$ | 0.62 (0.57, 0.66) |

[a]Ratio of Day 6/7 (during ciprofloxacin dosing) to Day 1/2 (pre-ciprofloxacin dosing)
[b]To be labeled equivalent, the 90% confidence interval for the geometric mean ratio must fall entirely between 0.8 and 1.25.

Example 2

In Vitro-In Vivo Extrapolation (IVIVE) Studies

In vitro data have been shown to be useful for the simulation of in vivo drug-drug interactions [Ito et al., *Drug Metabolism and Disposition* 33(6): 837-844 (2005); Karjalainen et al., Basic and Clinical Pharmacology & Toxicology 103: 157-165 (2008); McGinnity et al., *Drug Metabolism and Disposition* 36(6): 1126-1134 (2008); Zhang et al., *Acta Pharmacol Sin* 29(12): 1507-1514 (2008)]. In brief, the process involves combining in vitro knowledge regarding the properties of a potential inhibitor [$IC_{50}$ values for various cytochrome P450 (CYP) enzymes] with the in vitro knowledge regarding the pathways of metabolism of a given substrate (fraction metabolized by various CYP enzymes). So called in vitro-in vivo extrapolations (IVIVE) allow for the modeling of predicted changes in substrate drug AUC ($\Delta AUC$) values secondary to drug-drug interactions [McGinnity et al., *Drug Metabolism and Disposition* 36(6): 1126-1134 (2008)]. The results of IVIVE simulations conducted for pirfenidone are provided below and were compared to actual data from Example 1.

Ciprofloxacin-Pirfenidone IVIVE Simulations

Using the results of in vitro data for ciprofloxacin and hypothetical combinations of the fraction of pirfenidone metabolized by various CYP enzymes, the predicted ratio of the pirfenidone AUC before and during administration of ciprofloxacin were simulated. This was performed using Equation 1 below [taken from McGinnity et al., *Drug Metabolism and Disposition* 36(6): 1126-1134 (2008)]:

$$\Delta AUC = \frac{1}{\sum_{x=1}^{n}\left(\frac{fmx}{1+[I]in,u/Kix}\right) + \left(1 - \sum_{x=1}^{n} fmx\right)}$$

Equation 1

Where, $[I]_{in,u}$ is the free-drug concentration of the inhibitor (e.g., ciprofloxacin) entering the liver, $K_{ix}$ is the $K_i$ for ciprofloxacin for a given CYP and $fm_x$ is the fraction of the substrate drug (pirfenidone) metabolized by that CYP enzyme. The estimates for $[I]_{in,u}$ and $K_{ix}$ were taken from McGinnity et al. [*Drug Metabolism and Disposition* 36(6): 1126-1134 (2008)], while the estimates of $fm_x$ were varied based on possible scenarios for pirfenidone based on existing in vitro data.

In these simulations, using hypothetical combinations of the fraction of pirfenidone metabolized by various CYP enzymes, the predicted $\Delta AUC$ for pirfenidone with concomitant ciprofloxacin administration were simulated. The estimates for $[I]_{in,u}$ and $K_{ix}$ were taken from Zhang et al. [*Acta Pharmacol Sin* 29(12): 1507-1514 (2008)]. The results of the simulations for a ciprofloxacin dose of 750 mg BID, utilizing the "base case" and higher fractions metabolized are provided below in Table 3.

TABLE 3

Predicted impact of the 750 mg dose of ciprofloxacin co-administration on pirfenidone PK under several assumption scenarios for pirfenidone fraction metabolized by CYP1A2

| CYP | $[I]_{in,u}$ | $K_i$ | fm | |
|---|---|---|---|---|
| Base Case | | | | |
| 1A2 | 78 | 67.5 | 0.48 | |
| 2C9 | 78 | 90 | 0.0925 | |
| 2C19 | 78 | 500 | 0.0925 | |
| 2D6 | 78 | 500 | 0.0925 | |
| 2E1 | | | 0.0925 | |
| Predicted $\Delta AUC$ ($fm_{1A2}$ = 0.48) | | | | 1.48 |
| Postulated Predominance of CYP1A2 - 0.70 | | | | |
| 1A2 | 78 | 67.5 | 0.70 | |
| 2C9 | 78 | 90 | 0.0375 | |
| 2C19 | 78 | 500 | 0.0375 | |
| 2D6 | 78 | 500 | 0.0375 | |
| 2E1 | | | 0.0375 | |
| Predicted $\Delta AUC$ ($fm_{1A2}$ = 0.70) | | | | 1.67 |
| Postulated Predominance of CYP1A2 - 0.75 | | | | |
| 1A2 | 78 | 67.5 | 0.75 | |
| 2C9 | 78 | 90 | 0.025 | |
| 2C19 | 78 | 500 | 0.025 | |
| 2D6 | 78 | 500 | 0.025 | |
| 2E1 | | | 0.025 | |
| Predicted $\Delta AUC$ ($fm_{1A2}$ = 0.75) | | | | 1.73 |
| Postulated Predominance of CYP1A2 - 0.80 | | | | |
| 1A2 | 78 | 67.5 | 0.80 | |
| 2C9 | 78 | 90 | 0.0125 | |
| 2C19 | 78 | 500 | 0.0125 | |
| 2D6 | 78 | 500 | 0.0125 | |
| 2E1 | | | 0.0125 | |
| Predicted $\Delta AUC$ ($fm_{1A2}$ = 0.80) | | | | 1.78 |

The results of the simulations for ciprofloxacin doses of 250 or 500 mg BID utilizing $fm_{1A2}$ assumptions of 48% and 75% are provided below in Table 4; the only difference in the assumptions for these simulations is the lower $[I]_{in,u}$ due to the lower dose. This lower dose of ciprofloxacin would be expected to result in less of an effect on pirfenidone clearance. The predicted mean fold-change in pirfenidone AUC is 1.20-1.28 and 1.35-1.52 for dose of 250 mg BID and 500 mg BID, respectively, depending on assumptions for the fraction of pirfenidone metabolized by CYP1A2 in vivo.

TABLE 4

Predicted impact of the 250 or 500 mg dose of ciprofloxacin co-administration on pirfenidone PK under several assumption scenarios for pirfenidone fraction metabolized by CYP1A2

| CYP | $[I]_{in,u}$ | $K_i$ | fm | |
|---|---|---|---|---|
| Base Case (Ciprofloxacin 250 mg BID) | | | | |
| 1A2 | 52 | 67.5 | 0.48 | |
| 2C9 | 52 | 90 | 0.0925 | |
| 2C19 | 52 | 500 | 0.0925 | |
| 2D6 | 52 | 500 | 0.0925 | |
| 2E1 | | | 0.0925 | |
| Predicted $\Delta AUC$ ($fm_{1A2}$ = 0.48) | | | | 1.20 |

TABLE 4-continued

Predicted impact of the 250 or 500 mg dose of ciprofloxacin co-administration on pirfenidone PK under several assumption scenarios for pirfenidone fraction metabolized by CYP1A2

| CYP | $[I]_{in, u}$ | $K_i$ | fm |
|---|---|---|---|
| Postulated Predominance of CYP1A2 - 0.75 (Ciprofloxacin 250 mg BID) | | | |
| 1A2 | 52 | 67.5 | 0.70 |
| 2C9 | 52 | 90 | 0.0375 |
| 2C19 | 52 | 500 | 0.0375 |
| 2D6 | 52 | 500 | 0.0375 |
| 2E1 | | | 0.0375 |
| Predicted ΔAUC ($fm_{1A2}$ = 0.70) | | | 1.28 |
| Base Case (Ciprofloxacin 500 mg BID) | | | |
| 1A2 | 52 | 67.5 | 0.75 |
| 2C9 | 52 | 90 | 0.025 |
| 2C19 | 52 | 500 | 0.025 |
| 2D6 | 52 | 500 | 0.025 |
| 2E1 | | | 0.025 |
| Predicted ΔAUC ($fm_{1A2}$ = 0.75) | | | 1.35 |
| Postulated Predominance of CYP1A2 - 0.75 (Ciprofloxacin 500 mg BID) | | | |
| 1A2 | 52 | 67.5 | 0.80 |
| 2C9 | 52 | 90 | 0.0125 |
| 2C19 | 52 | 500 | 0.0125 |
| 2D6 | 52 | 500 | 0.0125 |
| 2E1 | | | 0.0125 |
| Predicted ΔAUC ($fm_{1A2}$ = 0.80) | | | 1.52 |

Hypothetical Inhibition of CYPs other than CYP1A2

Simulations were also run to predict the potential for drug-drug interactions with concomitant inhibitors of CYPs other than CYP1A2 such as CYP2C9, 2C19, 2D6, and 2E1. Given the fact that these other CYPs contribute to a smaller fraction of the in vivo metabolism of pirfenidone, hypothetical scenarios were simulated in which a drug had the theoretical ability to completely shut down one or more of CYP2C9, 2C19, 2D6, and 2E1. As shown in Table 5, complete inhibition of all four of these CYPs would only be predicted to result in an 8% increase in pirfenidone AUC. Inhibition of only one of these complementary pathways would not be expected to result in any increase in pirfenidone AUC. Note that these simulations assume that CYP1A2 is fully functional.

TABLE 5

Predicted impact of a hypothetical inhibitor of CYP2C9, 2C19, 2D6, and/or 2E1 on the PK exposure to pirfenidone with concomitant administration

| CYP | $[I]_{in, u}$ | $K_i$ | fm |
|---|---|---|---|
| Inhibition of All 4 Complementary CYPs | | | |
| 1A2 | 2.2 | 5000 | 0.75 |
| 2C9 | 2.2 | 0.0001 | 0.025 |
| 2C19 | 2.2 | 0.0001 | 0.025 |
| 2D6 | 2.2 | 0.0001 | 0.025 |
| 2E1 | 2.2 | 0.0001 | 0.025 |
| Predicted ΔAUC ($fm_{1A2}$ = 0.75) | | | 1.08 |
| Inhibition of 3 of the 4 Complementary CYPs | | | |
| 1A2 | 2.2 | 5000 | 0.75 |
| 2C9 | 2.2 | 0.0001 | 0.025 |
| 2C19 | 2.2 | 0.0001 | 0.025 |
| 2D6 | 2.2 | 0.0001 | 0.025 |
| 2E1 | 2.2 | 5000 | 0.025 |
| Predicted ΔAUC ($fm_{1A2}$ = 0.75) | | | 1.05 |

TABLE 5-continued

Predicted impact of a hypothetical inhibitor of CYP2C9, 2C19, 2D6, and/or 2E1 on the PK exposure to pirfenidone with concomitant administration

| CYP | $[I]_{in, u}$ | $K_i$ | fm |
|---|---|---|---|
| Inhibition of 2 of the 4 Complementary CYPs | | | |
| 1A2 | 2.2 | 5000 | 0.75 |
| 2C9 | 2.2 | 0.0001 | 0.025 |
| 2C19 | 2.2 | 0.0001 | 0.025 |
| 2D6 | 2.2 | 5000 | 0.025 |
| 2E1 | 2.2 | 5000 | 0.025 |
| Predicted ΔAUC ($fm_{1A2}$ = 0.75) | | | 1.03 |
| Inhibition of 1 of the 4 Complementary CYPs | | | |
| 1A2 | 2.2 | 5000 | 0.75 |
| 2C9 | 2.2 | 0.0001 | 0.025 |
| 2C19 | 2.2 | 5000 | 0.025 |
| 2D6 | 2.2 | 5000 | 0.025 |
| 2E1 | 2.2 | 5000 | 0.025 |
| Predicted ΔAUC ($fm_{1A2}$ = 0.75) | | | 1.00 |

Implications of IVIVE Simulation Results

Ciprofloxacin blocks only one, albeit major, pathway of pirfenidone metabolism (CYP1A2). A comprehensive review of all the relevant in vitro and in vivo data for pirfenidone coupled with IVIVE simulations suggests that CYP1A2 is responsible for 70-80% of the in vivo metabolism of pirfenidone (As shown in Table 6). IVIVE simulations in which a significantly lower or higher fraction metabolized by CYP1A2 were assumed resulted in ΔAUC predictions that were inconsistent with the observed AUC ratios in a Phase 1 clinical trial (see Example 1).

TABLE 6

Comparison of IVIVE simulation results with observations from a Phase 1 drug-drug interaction study (described in Example 1)

| Interacting Drug | Source | $fm_{1A2}$ | ΔAUC |
|---|---|---|---|
| Ciprofloxacin | IVIVE | 0.48 | 1.48 |
| | | 0.70 | 1.67 |
| | | 0.75 | 1.73 |
| | | 0.80 | 1.78 |
| | Clinical study (Example 1) | — | 1.81 |

While the present disclosure has been described in terms of various embodiments and examples, it is understood that variations and improvements will occur to those skilled in the art.

What is claimed is:

1. An improved method of administering pirfenidone therapy to treat a patient suffering from a fibrotic disorder, inflammatory disorder, or autoimmune disorder comprising reducing the dosage of pirfenidone administered to the patient by about one-half to about one-third during concomitant administration of ciprofloxacin at a dose of 750 mg twice daily (1500 mg/day).

2. A method of administering pirfenidone therapy to treat a patient suffering from a fibrotic disorder, inflammatory disorder, or autoimmune disorder, comprising administering to the patient a therapeutically effective amount of pirfenidone, and avoiding concomitant administration of ciprofloxacin at a dose of 750 mg.

3. The method of claim 1 wherein the pirfenidone dosage is reduced from about 2403 mg/day to a dosage ranging from about 1400 mg/day to about 1650 mg/day, optionally 1602 mg/day, during ciprofloxacin administration.

4. The method of claim 1 wherein the pirfenidone dosage is reduced from about 1800 mg/day to a dosage ranging from about 1000 mg/day to about 1250 mg/day, optionally 1200 mg/day, during ciprofloxacin administration.

5. The method of claim 1 wherein the method is for avoiding the potential for a reduced clearance of pirfenidone or the potential for an increased exposure to pirfenidone.

6. The pirfenidone of claim 1 wherein the total daily dose of pirfenidone is administered to the patient in divided doses three times per day, with food.

7. The method of claim 1 wherein the pirfenidone is administered in unit dosage forms that are capsules or tablets.

8. The method of claim 7 wherein the amount of pirfenidone in the unit dosage form is 200 mg or 267 mg.

9. The method of claim 1 wherein during concomitant ciprofloxacin administration 534 mg of pirfenidone is administered to the patient three times per day, with food.

10. The method of claim 1 wherein during the concomitant administration of ciprofloxacin the pirfenidone is administered at a total daily dosage of 1602 mg.

11. The method of claim 1 wherein during concomitant ciprofloxacin administration the pirfenidone is administered at a total daily dosage of about 1600 mg.

12. The method of claim 1 wherein the patient has idiopathic pulmonary fibrosis (IPF).

13. An improved method of administering pirfenidone therapy to treat a patient comprising reducing the dosage of pirfenidone administered to the patient by about one-half to about one-third during concomitant administration of ciprofloxacin at a dose of 750 mg twice daily (1500 mg/day), wherein the patient suffers from a disease selected from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, Hermansky-Pudlak syndrome, neurofibromatosis, diabetic retinopathy, skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis, hepatic fibrosis; acute or chronic renal disease; renal fibrosis; diabetic nephropathy; irritable bowel syndrome; pyresis; restenosis; cerebral malaria; stroke or ischemic injury; neural trauma; Huntington's disease; Parkinson's disease; acute or chronic pain; allergic rhinitis, allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, osteoporosis, multiple myeloma-related bone disorders; metastatic breast carcinoma, colorectal carcinoma, graft-versus-host reaction; multiple sclerosis, lupus, fibromyalgia; AIDS, viral diseases, Herpes Zoster, Herpes Simplex I or II, influenza virus, Severe Acute Respiratory Syndrome (SARS) cytomegalovirus; diabetes mellitus, acute myelogenous leukemia, chronic myelogenous leukemia, Kaposi's sarcoma, metastatic melanoma, multiple myeloma, breast cancer, colorectal carcinoma; gastric cancer; non-small cell lung cancer (NSCLC); bone metastases; neuromuscular pain, headache, cancer pain, dental pain, or arthritis pain; solid tumor angiogenesis, ocular neovascularization, infantile hemangioma; organ hypoxia; thrombin-induced platelet aggregation; or protozoal diseases.

14. The method of claim 10 wherein the patient has idiopathic pulmonary fibrosis (IPF).

15. The method of claim 10 wherein the patient suffers from a disease selected from idiopathic pulmonary fibrosis, pulmonary fibrosis, bronchiolitis obliterans, chronic lung transplant rejection, scleroderma, primary focal segmental glomerulosclerosis (FSGC) or membranoproliferative glomerulonephritis (MPGN), idiopathic interstitial pneumonia, interstitial lung disease in systemic sclerosis, a fibrosis condition of the lung, myocardiac fibrosis, musculoskeletal fibrosis, post-surgical adhesions, renal fibrotic disease, fibrotic vascular disease, Hermansky-Pudlak syndrome, neurofibromatosis, lymph node fibrosis associated with HIV, inflammatory pulmonary fibrosis, pancreatic fibrosis; hepatic fibrosis; or renal fibrosis.

16. The method of claim 14 wherein the total daily dose of pirfenidone is administered to the patient in divided doses three times per day.

17. The method of claim 16 wherein the pirfenidone is administered with food.

18. The method of claim 13 wherein during concomitant ciprofloxacin administration the pirfenidone is administered at a total daily dosage of 1602 mg.

* * * * *